United States Patent [19]

Edington et al.

[11] Patent Number: 4,467,091
[45] Date of Patent: Aug. 21, 1984

[54] ACYL AMINO PYRIDINES

[75] Inventors: Edwin T. Edington, Cookham; Alan C. White, Windsor, both of England

[73] Assignee: John Wyeth & Brother Limited, Maidenhead, England

[21] Appl. No.: 461,848

[22] Filed: Jan. 28, 1983

Related U.S. Application Data

[60] Division of Ser. No. 51,100, Jun. 22, 1979, abandoned, which is a continuation-in-part of Ser. No. 873,192, Jan. 30, 1978, Pat. No. 4,180,670.

[30] Foreign Application Priority Data

Feb. 2, 1977 [GB] United Kingdom ................. 4354/77
Jul. 9, 1977 [GB] United Kingdom ............... 28879/77

[51] Int. Cl.³ ................. C07D 495/04; C07D 471/04; C07D 213/75; A61K 31/44
[52] U.S. Cl. ..................................... 546/285; 546/77; 546/79; 546/80; 546/81; 546/93; 546/270; 546/274
[58] Field of Search ....................... 546/81, 93, 80, 79, 546/77, 274, 285, 270

[56] References Cited

PUBLICATIONS

Mndzhoyan, et al., "Amdes of the Pyridine and Thiazole Series", Chemical Abstracts 52:4641a.

Primary Examiner—Henry R. Jiles
Assistant Examiner—Dale A. Bjorkman
Attorney, Agent, or Firm—Arthur E. Wilfond

[57] ABSTRACT

Novel N-(4-pyridyl)acetamide derivatives having the formula

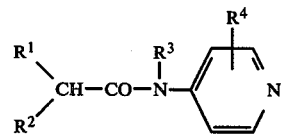

[where $R^1$ and $R^2$ are aryl or heteroarly (optionally linked together by a lower alkylene bridge) or one of $R^1$ and $R^2$ is aryl or heteroaryl and the other of $R^1$ and $R^2$ is lower alkyl or ar(lower)alkyl, $R^3$ and $R^4$ are each hydrogen or lower alkyl] and their nontoxic acid addition salts are described. They are chemical intermediates for the preparation of 4-pyridinamine derivatives having the formula

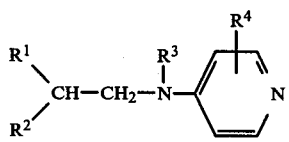

which show CNS activity and may be used as antidepressant drugs.

2 Claims, No Drawings

ACYL AMINO PYRIDINES

This application is a division of application Ser. No. 51,100 filed June 22, 1979, now abandoned, which is a continuation-in-part of application Ser. No. 873,192 filed Jan. 30, 1978, now U.S. Pat. No. 4,180,670.

The invention relates to novel N-(4-pyridyl) acetamide derivatives useful as chemical intermediates for the preparation of pharmaceutically active 4-aminopyridine derivatives.

The invention provides novel compounds having the formula I

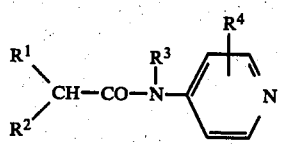

and their acid addition salts, wherein $R^1$ and $R^2$ together represent -$Ar^1$-(lower alkylene)-$Ar^2$- where $Ar^1$ and $Ar^2$ are independently arylene or heteroarylene, or when $R^1$ and $R^2$ are separate, one of $R^1$ and $R^2$ represents aryl or heteroaryl and the other one of $R^1$ and $R^2$ represents aryl, heteroaryl, ar(lower)alkyl or lower alkyl and $R^3$ and $R^4$ are independently hydrogen or lower alkyl.

By the term "lower" as used herein in connection with such groups as alkyl, alkylene and alkoxy, there is meant that the group contains up to 6 carbon atoms, preferably up to 4 carbon atoms. By the term "aryl or heteroaryl" there is meant a monovalent group having aromatic character. By the term "arylene or heteroarylene" there is meant a divalent group having aromatic character. The groups having aromatic character may be carbocyclic or heterocyclic and the aromatic ring or rings may be unsubstituted or carry one or more substituents.

$R^1$ and $R^2$ may be the same or different aromatic groups. Examples of aryl groups include phenyl; naphthyl phenyl substituted by one or two substituents, for example, halogen, for instance, fluorine, chlorine or bromine; lower alkyl, for instance, methyl, ethyl, propyl or butyl; lower alkoxy, for instance methoxy, ethoxy, propoxy or butoxy; lower alkylenedioxy, for instance methylenedioxy and trihaloalkyl, for instance, trifluoromethyl. The aryl group preferably has a monocyclic aromatic ring but may be bicyclic, for instance, naphthyl or naphthyl carrying one or more substituents, for example, those mentioned above in connection with substitution of phenyl. Examples of heteroaryl groups include furyl (for example, 3-furyl), thienyl (for example, 2-thienyl), oxazolyl, thiazolyl, benzthiazolyl, pyridyl (for example 2- and 4-pyridyl), quinolyl (for example 2-quinolyl) and isothiazolyl (for example, 5-isothiazolyl). The heteroaryl groups may be unsubstituted or substituted as described above for the substitution of phenyl. Preferred heteroaryl groups are thienyl, pyridyl and furyl.

One of $R^1$ and $R^2$ may be an aryl or heteroaryl group as described above whilst the other of $R^1$ and $R^2$ may be lower alkyl, for example, methyl, ethyl, propyl, butyl or pentyl, or ar(lower)alkyl, for instance, phen(lower)alkyl, e.g. benzyl or phenethyl. When $R^1$ and $R^2$ are connected together the two arylene or heteroarylene groups may be the same or different. The groups may be divalent groups corresponding to the aryl and heteroaryl groups particularly described above, for instance, phenylene.

When $R^1$ and $R^2$ are linked together they may represent a divalent group having the formula

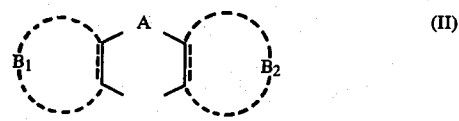

wherein A is alkylene of 1 to 4 carbon atoms and each of $B_1$ and $B_2$ together with the two carbon atoms attached thereto independently represents arylene or heteroarylene. The dotted lines in formula II in the rings are intended to indicate the aromatic character of the rings. The arylene and heteroarylene groups may be phenylene; phenylene substituted by one to two substituents selected from halogen, lower alkyl, lower alkoxy, lower alkylenedioxy and trifluoromethyl; naphthalene; pyridine-diyl and thiophene-diyl. Examples include o-phenylene, o-phenylene substituted as aforesaid, thiophene-2,3-diyl or thiophene-3,4-diyl.

The alkylene group of 1 to 4 carbon atoms represented by A in formula II may be a straight chain, for instance, methylene, dimethylene or trimethylene or may be branched, for example, a group having the formula —C(CH$_3$)$_2$—CH$_2$—.

$R^3$ and $R^4$ may be the same or different and are selected from hydrogen and lower alkyl, for example, methyl, ethyl, propyl and butyl. $R^3$ and $R^4$ are preferably chosen from hydrogen and methyl.

The acid addition salts may be formed from inorganic acids and organic acids and examples include the sulphate, hydrochloride, hydrobromide, hydroiodide, nitrate, phosphate, sulphonate (such as the methane sulphonate and toluene-p-sulphonate), acetate, maleate, fumarate, tartrate and formate.

It will be apparent to the reader that the compounds having formula I where $R^1$ and $R^2$ differ possess an asymmetric carbon atom and thus exhibit the property of optical isomerism. The invention includes the individual optical isomers as well as the racemic mixtures. The racemates may be resolved into individual optical isomers in known manner.

The compounds of general formula I and their acid addition salts can be prepared in manner known per se. In particular an amine having the formula

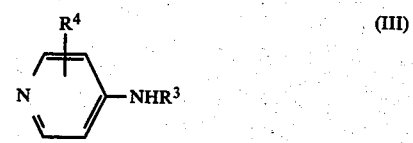

(where $R^3$ and $R^4$ are as defined above) is acylated to introduce the acyl group

(where $R^1$ and $R^2$ are as defined above). The acylation may be performed using the acyl halide, for instance, the acyl chloride or acyl bormide, in the presence of a suitable base. The starting materials for the acylation can be prepared by standard methods.

The compounds having formula I and their acid addition salts may be reduced so as to form 4-aminopyridine derivatives having the formula V

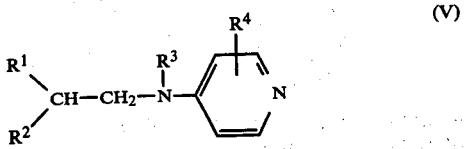

(wherein $R^1$, $R^2$, $R^3$ and $R^4$ are as defined above). The reduction may be carried out under conditions known for the reduction of amides to form amines. As reducing agent there may be used lithium aluminium hydride or diborane.

The compounds having formula V and their pharmaceutically acceptable acid addition salts are indicated for pharmaceutical use. In particular they show CNS (central nervous system) activity, when tested on warm blooded animals. They reverse the hypothermia induced by reserpine on mice and thus may be used as antidepressent drugs. The reduction product of Example 1 was active in reversing hypothermia induced by reserpine in mice at a dose of 5 mg/kg p.o. and the reduction product of Example 2 was active at 100 mg/kg p.o.

The following Examples illustrate the invention:

EXAMPLE 1

N-(2,2-diphenylethyl)4-pyridinamine

Diborane (generated from 0.033 moles $NaBH_4$ and 0.06 moles $BF_3/Et_2O$) was swept by a stream of nitrogen into a flask containing 2.16 grams (7.5 millimoles) of N-(4-pyridyl)diphenyl acetamide in 50 milliliters of dry tetrahydrofuran stirred and cooled to 0° C. When all diborane had been formed, the reaction mixture was heated under reflux for 3 hours and then left overnight at room temperature. The mixture was cooled to 0° C. and 10 millilitres of 6N hydrochloric acid was added. The tetrahydrofuran was removed at atmosphere pressure. The product was neutralised with 5N sodium hydroxide, extracted into ether, dried ($MgSO_4$) and evaporated to an oil which solidified. After trituration with ether, 1.46 g (71% yield) of fine felted needles were obtained. The title compound was converted to its hydrochloride by solution in isopropyl alcohol/HCl/$Et_2O$. 1.18 Grams of product m.p. 205°–207°, were obtained.

Analysis: Found C, 73.48%; H, 6.28%; N, 9.07%. $C_{19}H_{18}N_2$.HCl requires C, 73.56%; H, 6.16%; N, 9.03%.

The N-(4-pyridyl)diphenylacetamide starting material was prepared as follows:

9.4 Grams (0.1 mole) of 4-aminopyridine and 11.5 grams (0.05 mole) of diphenyl acetyl chloride were stirred together at room temperature in 65 milliliters of pyridine for 4.5 hours. The resulting mixture was poured into water and extracted with toluene. The organic phase was separated dried ($MgSO_4$) and the toluene removed. The resulting solid was recrystallised from toluene yielding 10.9 g 2,2-diphenyl-N-(4-pyridinyl)acetamide m.p. 166.5°–168° C. The fumarate salt was prepared by dissolving equimolar quantities of the free base and fumaric acid in hot 2-propanol and allowing the product to crystallise. Melting point 171°–173° C. Analysis: Found C, 68.2%; H, 5.25%; N, 6.7%. $C_{19}H_{16}N_2O.C_4H_4O_4$ requires: C, 68.3%; H, 5.0%; N, 6.7%.

EXAMPLE 2

N-[(10,11-dihydro-5H-dibenzo[a,d]-cyclohepten-5-yl)methyl]-4-pyridinamine

Diborane was generated by the dropwise addition over 1½ hours at room temperature of a solution of 1.14 grams (30 millimoles) of sodium borohydride in 30 c.c. of dry diglyme to a mixture of 6.2 c.c. (7.1 grams, 50 millimoles) of redistilled boron trifluoride etherate and 6.2 c.c. of dry diglyme. The evolved diborane was swept in a slow stream of dry nitrogen into a solution of 3.14 grams (10 millimoles) of N-[(10,11-dihydro-5H-dibenzo[a,d]cyclohepten-5-yl)carbonyl]-4-pyridinamine in 50 c.c. of dry tetrahydrofuran, cooled in ice. After complete addition of the borohydride solution, the generator flask was heated to 70°–80° for ½ hour to complete the generation of diborane, which was swept into the reduction mixture as before. The reduction mixture was stirred at 0° for a further hour and was then heated to reflux for 3 hours, maintaining the nitrogen atmosphere. The apparatus was then sealed and allowed to cool overnight. 6 Milliliters of 6N hydrochloric acid were then added dropwise with care to the reduction mixture, resulting in vigorous hydrogen evolution. The acid solution was the evaporated to dryness to remove tetrahydrofuran and the residue was treated with 25 c.c. of water, basified to pH9 with potassium carbonate, filtered, and the filtrate was extracted repeatedly with dichloromethane. The combined organic extracts were dried using $MgSO_4$ and evaporated, leaving 3.02 grams of a yellow oil whose IR spectrum contained no C=O absorption. This oil was taken up in a mixture of propan-2-ol, methanol and dichloromethane, made acid with ethereal hydrogen chloride, filtered and concentrated to 15 c.c. On cooling N-[(10,11-dihydro-5H-dibenzo[a,d]cyclohepten-5-yl)methyl]-4-pyridinamine, hydrochloride was deposited as colourless crystals (1.58 g, 42%), mp 245°–6° with effervescence. Analysis: Found C, 75.0%; H, 6.3%; N, 8.1%. $C_{21}H_{20}N_2$.HCl requires C, 74.9%; H, 6.3%; N, 8.3% The N-[(10,11-dihydro-5H-dibenzo[a,d]cyclohepten-5-yl)carbonyl]-4-pyridinamine starting material was prepared as follows:

A solution of 4.7 grams (50 milliliters) of 4-aminopyridine in 50 c.c. of dry pyridine was treated dropwise at room temperature with a solution of 6.6 grams of 10,11-dihydro-5H-dibenzo[a,d]cyclohepten-5-ylcarbonyl chloride. (M. A. Davis, Stanley O. Winthrop, J. Steward, F. A. Sunahara, and F. Herr, J. Medicin. Chem. 1963, 6, 251-5) in 50 c.c. of toluene. After the exothermic reaction subsided the mixture was stirred at room temperature for 4 hours and was then poured into 30 c.c. of water. 100 milliliters of toluene were added and the phases were separated. The toluene phase was washed once with 100 c.c. of water, then the combined aqueous phases were back-extracted with toluene (3×100 c.c.). The combined toluene solutions were dried ($MgSO_4$) and evaporated, leaving an oily residue which was evaporated several times with further toluene and finally once with ethanol to remove residual pyridine, giving 8.45 grams of a yellow solid. This solid was crystallised from toluene (charcoal) giving off-white crystals (4.78 g. 61%), mp 145°–6°; second crop, off-white crystals (0.96 g, 12%), mp 145°–7.5°.

Both crops were indicated by infrared spectroscopy to contain a trace of carboxylic acid (C=O at 1700 cm), so both fractions were combined, dissolved in toluene (150 c.c.) and washed with 2N sodium hydroxide solution (3×25 c.c.) water (3×25 c.c.) and saturated sodium chloride solution (2×25 c.c.), and dried (MgSO$_4$). The solution was filtered, concentrated to 50 c.c. and allowed to crystallise, giving 4.64 grams (57% yield) of N-[(10,11-dihydro-5H-dibenzo[a,d]cyclohepten-5-yl)carbonyl]-4-pyridinamine as colourless crystals, mp. 148°–9°.

Analysis: Found C, 80.5%; H, 6.0%; N, 9.0%. C$_{21}$H$_{18}$N$_2$O requires C, 80.2%; H, 5.8%; N, 8.9%.

EXAMPLE 3

The following acyl chlorides are reacted with the following amines in a manner similar to Examples 1 and 2 to give the products indicated.

| Acyl Chloride | Amine | Product |
| --- | --- | --- |
| Di(p-fluorophenyl)acetyl chloride | 2-Methyl-4-pyridinamine | 2,2-Di(p-fluorophenyl)-N—(2-methyl-4-pyridyl)-acetamide |
| Di(m-trifluorophenyl)acetyl chloride | 4-pyridinamine | N—(4-pyridyl)-2,2-di(m-trifluorophenyl)-acetamide |
| (3,4-Dichlorophenyl)phenyl acetyl chloride | 4-pyridinamine | 2-(3,4-dichlorophenyl)-2-phenyl-N—(4-pyridyl)-acetamide |
| 2-Phenylbutyryl chloride | 4-Pyridinamine | 2-Phenyl-N—(4-pyridyl)-butyramide |
| (β-Naphthyl)-(phenyl)acetyl dibride | 4-Pyridinamine | 2-(β-Naphthyl)-2-phenyl-N—(4-pyridyl)acetamide |
| (p-Ethoxyphenyl)-(m-toluyl)acetyl chloride | 4-Pyridinamine | 2-(p-Ethoxyphenyl)-N—(4-pyridyl)-2-(m-toluyl)acetamide |
| (3,4-Methylenedioxyphenyl)phenyl acetyl chloride | N—methyl-4-pyridinamine | N—Methyl-2-(3,4-methylenedioxyphenyl)-2-phenyl-N—(4-pyridyl) acetamide |
| (Phenyl)2-thienyl)acetylchloride | 4-Pyridinamine | 2-Phenyl-N—(4-pyridyl)-2-(2-thienyl)acetamide |
| (Phenyl)(2-pyridyl)acetyl chloride | 4-Pyridinamine | 2-Phenyl-2-(2-pyridyl)-N—(4-pyridyl)acetamide |
| 5,6,7,12-Tetrahydros-dibenzo[a,d]cyclo-octen-12-ylcarbonyl chloride | 4-Pyridinamine | N—[5,6,7,12-tetrahydro-dibenzo[a,d]-cycloocten-12-yl)carbonyl]-4-pyridinamine |
| 10,11-Dihydro-10,10-dimethyl-5H—benzo-[a,d]cyclohept-5-ylcarbonyl chloride | 2-Methyl-4-pyridinamine | N—(10,11-Dihydro-10,10-dimethyl-5H—benzo[a,d] cyclohept-5-yl)carbonyl]-2-methyl-4-pyridinamine |
| 4,9-Dihydro-naphtho[2,3-c]thien-4-ylcarbonyl chloride | N—methyl-4-pyridinamine | N—[(4,9-Dihydro-naphtho[2,3-c]-thien-4-yl)carbonyl]-N—methyl-4-pyridinamine |
| 5,10-Dihdro-benzo[g]quinol-10-ylcarbonyl chloride | 4-Pyridinamine | N—[5,10-dihydro-benzo[g]quinol-10-yl)carbonyl]-4-pyridinamine |
| 7,12-Dihydro- | 4-Pyridin- | N—[(7,12-dihydro-benz |

-continued

| Acyl Chloride | Amine | Product |
| --- | --- | --- |
| benz[a]anthracen-7-ylcarbonyl chloride | amine | [a]anthracen-7-yl)carbonyl]-4-pyridinamine |
| 10,11-Dihydro-1-methyl-5H—dibenzo[a,d]cyclohepten-5-ylcarbonyl chloride | 4-Pyridinamine | N—[(10,11-dihydro-1-methyl-5H—dibenzo[a,d]cyclohepten-5-yl)carbonyl]-4-pyridinamine |
| 10,11-Dihydro-2,3-dimethoxy-5H—dibenzo[a,d]cyclohept-5-ylcarbonyl chloride | 4-Pyridinamine | N—[(10,11-dihydro-2,3-dimethoxy-5H—dibenzo[a,d]cyclohepten-5-yl)carbonyl]-4-pyridinamine |
| 10,11-Dihydro-2,3-methylenedioxy-5H—dibenzo[a,d]cyclohept-5-ylcarbonyl chloride | 4-Pyridinamine | N—[(10,11-dihydro-2,3-methylenedioxy-5H—dibenzo[a,d]cyclohept-5-yl)carbonyl]-4-pyridinamine |
| 10,11-Dihydro-3-trifluoromethyl-5H—dibenzo[a,d]cyclohept-5-yl carbonyl chloride | 4-Pyridinamine | N—[10,11-dihydro-3-trifluoromethyl-5H—dibenzo[a,d]cyclohept-5-yl)carbonyl]-4-pyridinamine |

We claim:

1. A compound selected from those having the formula $$R^1\!\!\diagdown\!\!\!\underset{R^2\diagup}{CH}\!\!-\!\!CO\!\!-\!\!\underset{R^3}{N}\!\!-\!\!\!\!\diagup\!\!\!\!\!\diagdown\!\!\!\overset{R^4}{\diagdown}\!\!\!\!N$$

and their pharmaceutically acceptable acid addition salts, wherein $R^1$ and $R^2$ together represent a divalent group having the formula $$B_1\cdots\overset{A}{\diagdown}\cdots B_2$$

wherein A is alkylene of 1 to 4 carbon atoms and each of $B_1$ and $B_2$ together with the two carbon atoms attached thereto represents a member selected from the group consisting of phenylene; naphthylene; phenylene substituted by one to two substituents selected from halogen, lower alkyl, lower alkoxy, lower alkylenedioxy and trifluoromethyl; pyridinediyl and thiophenediyl, and $R^3$ and $R^4$ are independently selected from hydrogen and lower alkyl.

2. A compound as defined in claim 1, which is N-[(10,11-dihydro-5H-dibenzo[a,d]cyclohepten-5-yl)carbonyl]-4-pyridinamine or a pharmaceutical acceptable acid addition salt thereof.

* * * * *